(12) United States Patent
Zheng et al.

(10) Patent No.: US 12,304,879 B2
(45) Date of Patent: *May 20, 2025

(54) PREPARATION METHOD OF 1-CHLORO-2,3,3-TRIFLUOROPROPENE

(71) Applicant: ZIBO RHEMA INTERNATIONAL INC., Zibo (CN)

(72) Inventors: Farui Zheng, Zibo (CN); Yawei Zheng, Zibo (CN); Panming Jian, Zibo (CN); Zihan Zheng, Zibo (CN)

(73) Assignee: ZIBO RHEMA INTERNATIONAL INC., Zibo (CN)

( * ) Notice: Subject to any disclaimer, the term of this patent is extended or adjusted under 35 U.S.C. 154(b) by 472 days.

This patent is subject to a terminal disclaimer.

(21) Appl. No.: 17/799,927

(22) PCT Filed: Jan. 21, 2021

(86) PCT No.: PCT/CN2021/072972
§ 371 (c)(1),
(2) Date: Aug. 16, 2022

(87) PCT Pub. No.: WO2022/083017
PCT Pub. Date: Apr. 28, 2022

(65) Prior Publication Data
US 2023/0081584 A1    Mar. 16, 2023

(30) Foreign Application Priority Data

Oct. 20, 2020   (CN) .......................... 202011124655.1

(51) Int. Cl.
*C07C 17/20* (2006.01)
(52) U.S. Cl.
CPC .................................. *C07C 17/206* (2013.01)

(58) Field of Classification Search
CPC ........ C07C 17/206; C07C 17/25; C07C 21/18
See application file for complete search history.

(56) References Cited

U.S. PATENT DOCUMENTS 11,649,418 B2 * 5/2023 Zheng .................. C11D 7/5018
510/412

FOREIGN PATENT DOCUMENTS

| CN | 101028994 A | 9/2007 |
|---|---|---|
| CN | 101168494 A | 4/2008 |

(Continued)

*Primary Examiner* — Jafar F Parsa
(74) *Attorney, Agent, or Firm* — Bayramoglu Law Offices LLC

(57) ABSTRACT

A preparation method of 1-chloro-2,3,3-trifluoropropene is provided. As a new eco-friendly compound that makes up a heat transfer medium, the 1-chloro-2,3,3-trifluoropropene (HCFO-1233yd) has been valued in the field of industrial cleaning and explosion-proof due to it excellent performance of low global warming potential (GWP) and ozone depletion potential (ODP) values, but HCFO-1233yd has high preparation cost that limits its large-scale application. In the preparation method of the present disclosure, 1,1,2,3,3-pentachloropropane is fluorinated into 1,2-dichloro-3,3-difluoropropene under the catalysis of a chromium-containing solid catalyst. Under the catalysis with a chromium-based catalyst as a main catalyst, 1,2-dichloro-3,3-difluoropropene is fluorinated with a hydrogen fluoride (HF) gas phase to generate 1-chloro-2,3,3-trifluoropropene, which greatly reduces the production cost of 1-chloro-2,3,3-trifluoropropene, and involves a simple preparation process, high product selectivity, and high raw material conversion rate.

3 Claims, 2 Drawing Sheets

(56) References Cited

FOREIGN PATENT DOCUMENTS

| | | | |
|---|---|---|---|
| CN | 108383679 | A | 8/2018 |
| CN | 108473397 | A | 8/2018 |
| CN | 108473398 | A | 8/2018 |
| CN | 109970508 | A | 7/2019 |
| CN | 107250088 | B | 9/2019 |
| CN | 112125776 | A | 12/2020 |
| JP | 2017001990 | A | 1/2017 |
| JP | 2017014160 | A | 1/2017 |
| JP | 2017124997 | A | 7/2017 |
| WO | 2017110851 | A1 | 6/2017 |
| WO | 2019189024 | A1 | 10/2019 |
| WO | 2020026990 | A1 | 2/2020 |

\* cited by examiner

PREPARATION METHOD OF 1-CHLORO-2,3,3-TRIFLUOROPROPENE

CROSS REFERENCE TO THE RELATED APPLICATIONS

This application is the national phase entry of International Application No. PCT/CN2021/072972, filed on Jan. 21, 2021, which is based upon and claims priority to Chinese Patent Application No. 202011124655.1, filed on Oct. 20, 2020, the entire contents of which are incorporated herein by reference.

TECHNICAL FIELD

The present disclosure provides a preparation method of 1-chloro-2,3,3-trifluoropropene and belongs to the technical field of 1-chloro-2,3,3-trifluoropropene preparation.

BACKGROUND

As a new eco-friendly compound that makes up a heat transfer medium, 1-chloro-2,3,3-trifluoropropene (HCFO-1233yd) has been valued for its low global warming potential (GWP) and ozone depletion potential (ODP) values. However, in the field of industrial cleaning, in addition to the superior performance of low GWP and ODP values, the HCFO-1233yd has a high production cost, which directly limits the market acceptance of cleaning agents based on HCFO-1233yd.

In the published patent applications CN 109970508 A and CN 107250088 B for HCFO-1233yd production, 2,2,3,3-tetrafluoropropanol is chlorinated to produce 3-chloro-1,1,2,2-tetrafluoropropane (244ca). Then 244ca is subjected to dehydrofluorination to produce HCFO-1233yd. The raw material 2,2,3,3-tetrafluoropropanol is an extremely expensive compound in industrial production (about 90,000 yuan per ton), such that the production cost of HCFO-1233yd is greatly increased, which is undesirable to the cleaning agent and foaming agent markets.

In addition, the raw material 2,2,3,3-tetrafluoropropanol in the above-mentioned patents is a compound produced by alcoholization of tetrafluoroethylene (TFE), and thus the compound must be produced in a TFE production plant, which increases the difficulty of acquiring the compound and thus limits the industrial mass production of 1233yd.

SUMMARY

It is the expectation of the market to easily acquire low-cost raw materials to prepare HCFO-1233yd, such as to enable the mass production of HCFO-1233yd and greatly reduce the production cost.

The technical problem to be solved by the present disclosure is to overcome the deficiencies of the prior art and provide a preparation method of 1-chloro-2,3,3-trifluoropropene, which is simple and cost-effective and leads to a product with high purity.

The present disclosure adopts the following technical solutions to solve the technical problem: A preparation method of 1-chloro-2,3,3-trifluoropropene is provided, including the following steps: 1) subjecting 1,1,2,3,3-pentachloropropane ($CHCl_2$—CHCl—$CHCl_2$) to a reaction with hydrogen fluoride (HF) under the catalysis of a chromium-containing solid catalyst, such that the 1,1,2,3,3-pentachloropropane is fluorinated into 1,2-dichloro-3,3-difluoropropene (CHCl=CCl—$CHF_2$), where a reaction formula is as follows:

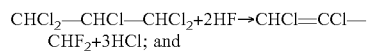
$CHCl_2$—CHCl—$CHCl_2$+2HF→CHCl=CCl—$CHF_2$+3HCl; and 2) fluorinating the 1,2-dichloro-3,3-difluoropropene into the 1-chloro-2,3,3-trifluoropropene (CHCl=CF—$CHF_2$) with an HF gas phase under the catalysis of a catalyst, where a reaction formula is as follows:

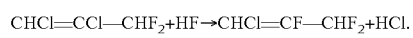
CHCl=CCl—$CHF_2$+HF→CHCl=CF—$CHF_2$+HCl.

The 1-chloro-2,3,3-trifluoropropene is successfully prepared through a two-step fluorination process with 1,1,2,3,3-pentachloropropane as a raw material. The 1,1,2,3,3-pentachloropropane is only 10,000 to 20,000 yuan per ton, which greatly reduces the cost compared with a process that uses 2,2,3,3-tetrafluoropropanol as a raw material in the prior art. In addition, the preparation method involves a simple fluorination process, high product selectivity, and high raw material conversion rate.

Preferably, in step 1), a gas-phase catalytic reaction may be adopted.

Preferably, when the gas-phase catalytic reaction is adopted, the reaction may be conducted at a temperature of 200° C. to 350° C. and a space velocity of 60 $h^{-1}$ to 570 $h^{-1}$. A molar ratio of the HF to the 1,1,2,3,3-pentachloropropane may be (5-25):1.

The above-mentioned reaction conditions can lead to high conversion rate and product selectivity for the 1,1,2,3,3-pentachloropropane.

The reaction may be conducted at a temperature of 275° C. and a space velocity of 240 $h^1$, and a molar ratio of the HF to the 1,1,2,3,3-pentachloropropane may be 15:1. Such reaction conditions can lead to the optimal product selectivity and raw material conversion rate.

Preferably, the chromium-containing solid catalyst in step 1) may be an F—$Cr_2O_3$-loaded activated carbon or zirconium oxychloride catalyst. The F—$Cr_2O_3$-loaded activated carbon or zirconium oxychloride catalyst can lead to the optimal catalytic effect for the reaction in step 1), thereby effectively improving the conversion rate of 1,1,2,3,3-pentachloropropane.

Preferably, the catalyst in step 2) may include a main catalyst and a cocatalyst. The main catalyst may be a chromium-based catalyst treated with HF, and the cocatalyst may be one or a mixture of two or more selected from the group consisting of Zn, Co, Ni, and Cu.

Preferably, in step 2), the reaction may be conducted at a temperature of 250° C. to 400° C. and a space velocity of 50 $h^{-1}$ to 550 $h^{-1}$, and a molar ratio of the HF to the 1,2-dichloro-3,3-difluoropropene may be (1-8):1.

Preferably, the reaction may be conducted at a temperature of 350° C. and a space velocity of 220 $h^{-1}$, and a molar ratio of the HF to the 1,2-dichloro-3,3-difluoropropene may be 4:1.

The above reaction conditions are most suitable for the fluorination of 1,2-dichloro-3,3-difluoropropene to produce 1-chloro-2,3,3-trifluoropropene, which can achieve the optimal raw material conversion rate and product selectivity.

Preferably, in the product 1,2-dichloro-3,3-difluoropropene obtained in step 1), the trans-form and the cis-form may coexist.

Preferably, in the product 1-chloro-2,3,3-trifluoropropene obtained in step 2), the trans-form and the cis-form may coexist.

The product 1-chloro-2,3,3-trifluoropropene obtained in step 2) is the main substance to be prepared in the present disclosure, in which the trans-form and the cis-form always coexist. However, boiling points of the two forms of 1-chloro-2,3,3-trifluoropropene are quite different, and thus rectification can be further conducted to obtain the two products of trans-1-chloro-2,3,3-trifluoropropene (HCFO-1233yd (E)) and cis-1-chloro-2,3,3-trifluoropropene (HCFO-1233yd (Z)).

Beneficial Effects:

Compared with the prior art, the present disclosure has the following beneficial effects: The 1-chloro-2,3,3-trifluoropropene is successfully prepared through a two-step fluorination process with 1,1,2,3,3-pentachloropropane as a raw material. The 1,1,2,3,3-pentachloropropane is only 10,000 to 20,000 yuan per ton, which greatly reduces the cost compared with the process in the prior art. In addition, the preparation method involves a simple fluorination process, high product selectivity, and high raw material conversion rate. In step 1), the conversion rate of 1,1,2,3,3-pentachloropropane can reach about 100%, and the selectivity for the product 1,2-dichloro-3,3-difluoropropene can reach 91.2%. In step 2), the conversion rate of 1,2-dichloro-3,3-difluoropropene can reach 69%, and the selectivity for the product 1-chloro-2,3,3-trifluoropropene can reach 78%. In addition, 1,1,2,3,3-pentachloropropane is in a liquid state at room temperature, and thus is easy to transport and store without flammable and explosive hazards, which greatly reduces the potential safety hazard in production.

DETAILED DESCRIPTION OF THE EMBODIMENTS

Example 4 is the optimal example of the present disclosure, and the present disclosure will be further described below with reference to the examples.

The 1,1,2,3,3-pentachloropropane (CHCl$_2$—CHCl—CHCl$_2$) and HF used in the following examples are produced by Ningxia Purui Chemical Co., Ltd., and the catalysts are all produced by Shandong Zibo Feiyuan Chemical Co., Ltd.

Example 1 A preparation method of 1-chloro-2,3,3-trifluoropropene was provided, including the following steps:
1) 1,1,2,3,3-pentachloropropane (CHCl$_2$—CHCl—CHCl$_2$) (HCC-240da) and an HF gas were subjected to a gas-phase catalytic reaction at a space velocity of 240 h$^{-1}$ under the catalysis of a F—Cr$_2$O$_3$ catalyst to produce 1,2-dichloro-3,3-difluoropropene (HCFO-1232aa), where a ratio of HF to HCC-240da was 15:1; and a reaction formula was as follows:

CHCl$_2$—CHCl—CHCl$_2$+2HF→CHCl═CCl—CHF$_2$(E,Z)+3HCl

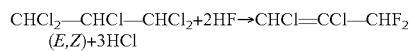

where (E, Z) means that the cis-form and the trans-form coexist in HCFO-1232aa; and 2) the 1,2-dichloro-3,3-difluoropropene and an HF gas were subjected to a fluorination reaction at a temperature of 350° C. and a space velocity of 220 h$^{-1}$ under the catalysis with Cr-loaded zirconium oxychloride treated by HF as a main catalyst and a mixture of Co and Zn as a cocatalyst to produce the 1-chloro-2,3,3-trifluoropropene, where a molar ratio of the HF to the 1,2-dichloro-3,3-difluoropropene was 4:1; and a reaction formula was as follows:

CHCl═CCl—CHF$_2$(E,Z)+HF→CHCl═CF—CHF$_2$(E,Z)+HCl, where (E, Z) means that the cis-form and the trans-form coexist in the 1-chloro-2,3,3-trifluoropropene. A corresponding relationship between the reaction temperature and the content of HCC-240da and HCFO-1232aa after the reaction in step 1) are shown in FIG. 1, where the content of HCC-240da and HCFO-1232aa are shown as percentages in the obtained system.

Figure 1:
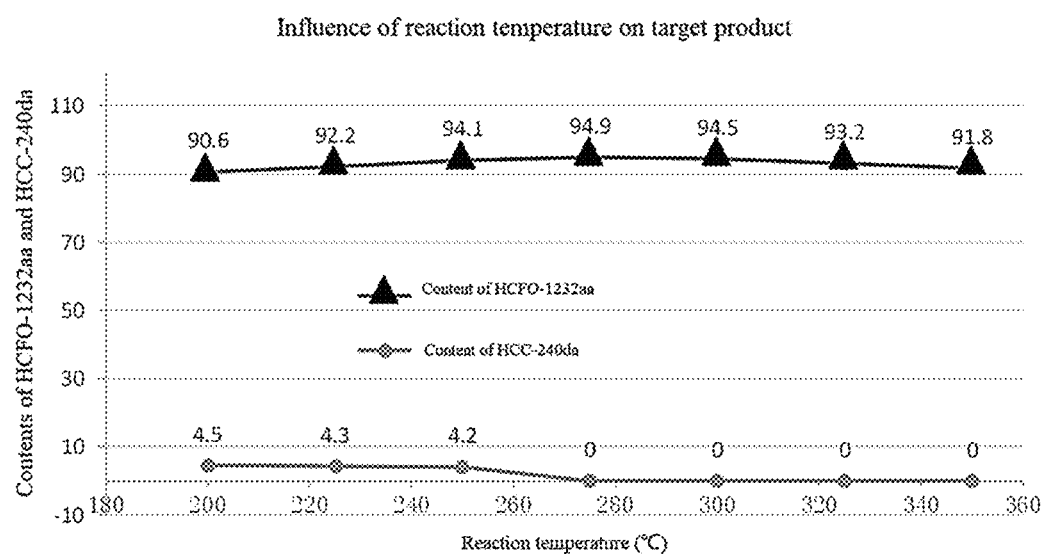
FIG. 1 shows the influence of different reaction temperatures on the content of HCC-240da and HCFO-1232aa in a reaction product in step 1).

As shown in FIG. 1, the maximum HCFO-1232aa content can be obtained at a reaction temperature of 275° C. under the same other conditions.

Examples 2 to 7 and Comparative Example 1

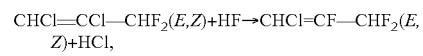

Preparation methods of 1-chloro-2,3,3-trifluoropropene were provided, where on the basis of Example 1, the reaction temperature in step 1) was set to 270° C., and the space velocity in step 1) was adjusted. Products obtained under different space velocities were tested for component content, conversion rate, and selectivity. A relationship between the space velocity and the reaction in step 1) for Examples 2 to 7 and Comparative Example 1 are shown in Table 1.

TABLE 1

Influence of the space velocity on the reaction in step 1)

| Example | Space velocity/ h$^{-1}$ | Contents of components in reaction product/(%) HCC-240da | Contents of components in reaction product/(%) HCFO-1232aa | HCC-240da conversion rate/(%) | HCFO-1232aa selectivity/(%) |
|---|---|---|---|---|---|
| Example 2 | 60 | 0.05 | 92.5 | 99.95 | 87.1 |
| Example 3 | 120 | 0.04 | 93.1 | 99.9 | 89.4 |
| Example 4 | 240 | 0.1 | 95.7 | 99.4 | 96.3 |
| Example 5 | 350 | 0.9 | 92.8 | 99.1 | 90.8 |
| Example 6 | 460 | 2.6 | 89.6 | 97.4 | 86.5 |
| Example 7 | 570 | 4.6 | 83.5 | 95.4 | 83.4 |
| Comparative Example 1 | 600 | 5.1 | 81.1 | 94.9 | 82.2 |

As shown in Table 1, when the space velocity is too low, the production efficiency is low and the product selectivity does not increase. When the space velocity is too high, the conversion rate and product selectivity will both decrease. Therefore, the optimal space velocity in step 1) is 240 h$^{-1}$ as shown in Table 1.

Examples 8 to 12 and Comparative Example 2 Preparation methods of 1-chloro-2,3,3-trifluoropropene were provided, where on the basis of Example 1, the reaction temperature in step 1) was set to 275° C., a feed amount of HCC-240da was 0.015 mL/min, O$_2$ was introduced during the reaction process at an amount 1% to 4% of a molar mass of HCC-240da, and a feed amount of HF was adjusted through an HF flow meter. Degrees of reaction under different feed ratios were tested. The oxygen was introduced to consume coke produced during the reaction process, such as to minimize the influence of carbon deposit on the deactivation of the catalyst.

Test results of HF feed rate, feed ratio, and conversion rate and selectivity after the reaction in step 1) are shown in Table 2.

TABLE 2

Influence of the feed ratio on the reaction in step 1)

| Example | HF (mL/min) | HF:HCC-240da (mol/mol) | HCC-240da conversion rate (%) | HCFO-1232aa selectivity (%) |
|---|---|---|---|---|
| Example 8 | 13.51 | 5 | 30.5 | 80.1 |
| Example 9 | 27.02 | 10 | 80.9 | 84.7 |
| Example 10 | 40.53 | 15 | 99.6 | 90.4 |
| Example 11 | 54.04 | 20 | 100 | 90.6 |
| Example 12 | 67.55 | 25 | 100 | 91.2 |
| Comparative Example 2 | 79.45 | 30 | 99.1 | 87.3 |

As shown in Table 2, when the HF feed amount is too high, the raw material conversion rate and product selectivity do not increase, but decrease to some extent, and a large amount of HF will be wasted. Therefore, it is determined that the optimal molar ratio of the HF to the 1,1,2,3,3-pentachloropropane was 15:1.

Example 13 Preparation methods of 1-chloro-2,3,3-trifluoropropene were provided, where on the basis of Example 1, the reaction temperature in step 1) was set to 275° C.

The reaction temperature in step 2) was set to 250° C. to 400° C. Cr-loaded zirconium oxychloride was adopted as a main catalyst, and one or more selected from the group consisting of Zn, Co, Ni, and Cu were adopted as a cocatalyst. The reaction effects under different temperatures and different cocatalysts were tested.

Figure 2:
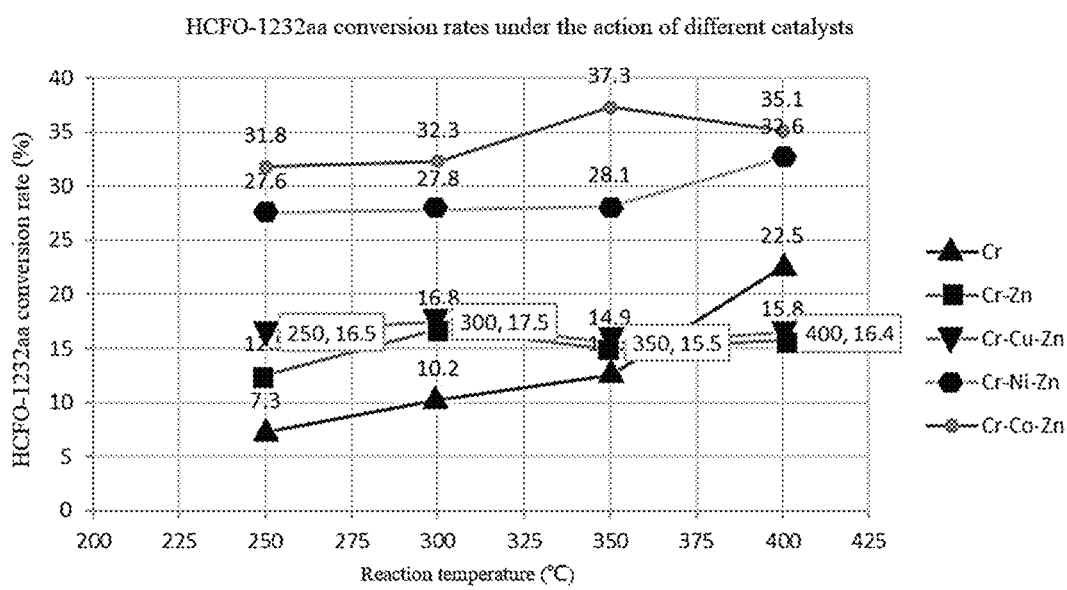
FIG. 2 shows the influence of different temperatures and different cocatalysts on the conversion rate of HCFO-1232aa in step 2).
Figure 3:
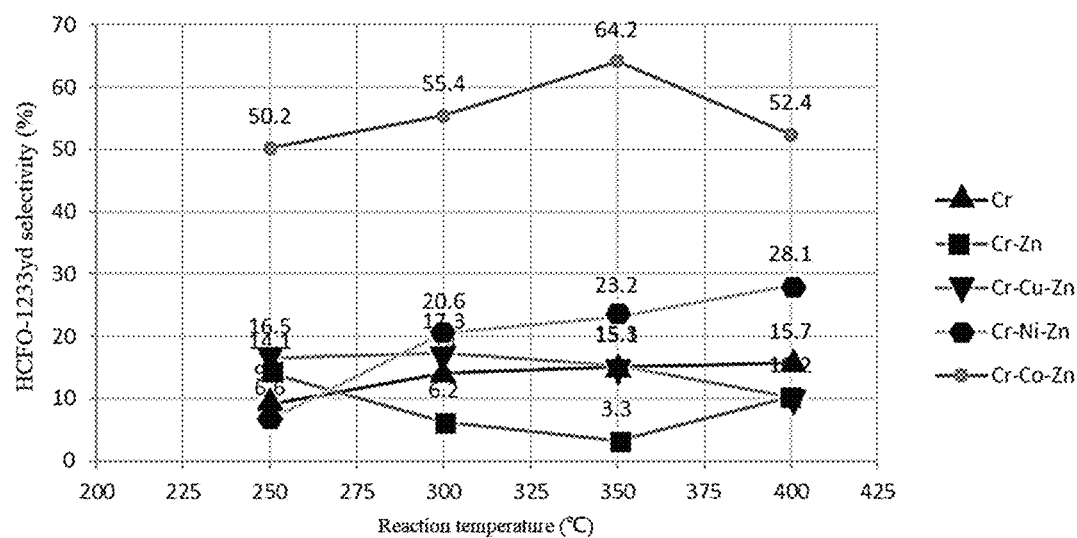
FIG. 3 shows the influence of different temperatures and different cocatalysts on the HCFO-1233yd selectivity in step 2).

The reaction effects under different temperatures and different cocatalysts are shown in FIG. 2 and FIG. 3. The conversion rate of HCFO-1232aa shown in FIG. 2 was calculated as follows: After the reaction was completed, a sample was collected to detect a residual amount of HCFO-1232aa in the raw material, and a proportion of the residual amount in the total feed amount was calculated. The selectivity for HCFO-1233yd shown in FIG. 3 referred to a proportion of 1-chloro-2,3,3-trifluoropropene in the total product after the reaction.

As shown in FIG. 2 and FIG. 3, the optimal reaction effect was achieved at 300° C. to 350° C. in step 2), and the Cr—Co—Zn catalyst led to the optimal catalytic effect. Therefore, it was recommended that Cr was used as a main catalyst and a mixture of Co and Zn was used as a cocatalyst to achieve the optimal catalytic efficiency. Moreover, the conversion rate of HCFO-1232aa was greater than 37.3% and the selectivity for HCFO1233yd was greater than 64.2% under the action of the catalyst Cr—Co—Zn at a reaction temperature of 350° C.

Examples 14 to 19 and Comparative Example 3 Preparation methods of 1-chloro-2,3,3-trifluoropropene were provided, where on the basis of Example 13, in step 2), Cr-loaded zirconium oxychloride treated by HF was used as a main catalyst, a mixture of Co and Zn was used as a cocatalyst, the reaction temperature was set to 350° C., and the space velocity was adjusted. The reaction effects at different space velocities in step 2) were tested.

The space velocities in step 2) and the product component content, conversion rate, and selectivity after the reaction in the examples and comparative example are shown in Table 3.

TABLE 3

Influence of the space velocity on the reaction in step 2)

| Example | Space velocity ($h^{-1}$) | Contents of main components in product (%) | | | HCFO-(%) conversion rate 1232aaD | HCFO-1233yd selectivity (%) |
|---|---|---|---|---|---|---|
| | | HCFO-1232aa | HCFO-1233yd | others | | |
| Example 14 | 50 | 35.12 | 33.61 | 31.27 | 64.88 | 40.67 |
| Example 15 | 110 | 39.14 | 36.65 | 24.21 | 60.68 | 55.16 |
| Example 16 | 220 | 41.9 | 40.59 | 13.5 | 58.09 | 65.76 |
| Example 17 | 330 | 56.48 | 30.81 | 12.71 | 43.52 | 68.68 |
| Example 18 | 450 | 68.41 | 22.63 | 8.96 | 31.59 | 69.49 |
| Example 19 | 550 | 80.46 | 15.51 | 4.03 | 19.54 | 75.37 |
| Comparative Example 3 | 600 | 86.53 | 12.25 | 2.22 | 14.47 | 80.65 |

As shown in Table 3, when the space velocity is too low, the production efficiency is low, the selectivity for the product HCFO-1233yd is low, and an impurity is easily generated through further reaction. When the space velocity is too high, with reference to Comparative Example 3, HCFO-1232aa does not participate in the reaction effectively, and the conversion rate is low. Therefore, as shown in Table 3, when the space velocity is 220 $h^{-1}$, the raw material conversion rate and the product selectivity can be both guaranteed to achieve the optimal reaction effect.

Examples 20 to 24 and Comparative Example 4 Preparation methods of 1-chloro-2,3,3-trifluoropropene were provided, where on the basis of Example 16, the feed amount of HCFO-1232aa was set to 0.033 mL/min, and the feed amount of HF was adjusted through an HF flow meter to determine the influence of the molar ratio of the materials in step 2) on the reaction effect.

The HF feed rate, the molar ratio, and the conversion rate and selectivity after the reaction in step 2) of the examples and comparative example are shown in Table 4, where HF:HCFO-1232aa is a molar ratio of the HF to the 1,2-dichloro-3,3-difluoropropene.

TABLE 4

Influence of the HF feed rate on the reaction result in step 2)

| Example | HF (mL/min) | HF:HCFO-1232aa (mol/mol) | HCFO-1232aa conversion rate (%) | HCFO-1233 yd selectivity (%) |
|---|---|---|---|---|
| Example 20 | 7.93 | 1 | 39.26 | 78.14 |
| Example 21 | 15.86 | 2 | 50.42 | 75.15 |
| Example 22 | 31.53 | 4 | 65.16 | 70.58 |
| Example 23 | 47.58 | 6 | 67.79 | 63.57 |
| Example 24 | 63.45 | 8 | 69.21 | 57.12 |
| Comparative Example 4 | 78.65 | 9 | 70.12 | 54.85 |

As shown in Table 4, in step 2), when the HF feed rate is too low, the reaction of HCFO-1232aa is insufficient, and the conversion rate is low. When the HF feed rate is too high, 1233yd easily further reacts to generate other substances, and the selectivity is reduced. Therefore, as shown in Table 4, when the HF feed rate is 31.53 mL/min, that is, when the molar ratio is 4:1, the conversion rate of HCFO-1232aa is 65.16%, and the selectivity for HCFO-1233yd is 70.58%, in which case the raw material conversion rate and the product selectivity are both guaranteed to achieve the optimal reaction effect.

The above are merely preferred examples of the present disclosure and are not intended to limit the present disclosure in other forms. Any person skilled in the art may make changes or modifications based on the technical contents disclosed above to obtain equivalent examples. Any simple amendments or equivalent changes and modifications made to the above examples according to the technical essence of the present disclosure without departing from the content of the technical solutions of the present disclosure should fall within the protection scope of the technical solutions of the present disclosure.

What is claimed is:

1. A preparation method of 1-chloro-2,3,3-trifluoropropene, comprising the following steps:
   1) subjecting 1,1,2,3,3-pentachloropropane to a reaction with hydrogen fluoride (HF) under a catalysis of a chromium-containing solid catalyst, wherein the 1,1,2,3,3-pentachloropropane is fluorinated into 1,2-dichloro-3,3-difluoropropene; the reaction is conducted at a temperature of 200° C. to 350° C., a space velocity of 60 $h^{-1}$ to 570 $h^{-1}$, and a molar ratio of the HF to the 1,1,2,3,3-pentachloropropane as (5-25): 1; and the chromium-containing solid catalyst is an F-$Cr_2O_3$-loaded activated carbon or zirconium oxychloride catalyst;
   2) fluorinating the 1,2-dichloro-3,3-difluoropropene into the 1-chloro-2,3,3-trifluoropropene with an HF gas phase under a catalysis of a catalyst, wherein the fluorinating is conducted at a temperature of 250° C. to 400° C., a space velocity of 50 $h^{-1}$ to 550 $h^{-1}$, and a molar ratio of the HF gas phase to the 1,2-dichloro-3,3-difluoropropene as (1-8): 1; the catalyst comprises a main catalyst and a cocatalyst; and the main catalyst is a chromium-based catalyst treated with HF, and the cocatalyst is one or a mixture of two or more selected from the group consisting of Zn, Co, Ni, and Cu.

2. The preparation method of the 1-chloro-2,3,3-trifluoropropene according to claim 1, wherein the reaction is conducted at a temperature of 275° C., a space velocity of 240 $h^{-1}$, and a molar ratio of the HF to the 1,1,2,3,3-pentachloropropane as 15:1.

3. The preparation method of the 1-chloro-2,3,3-trifluoropropene according to claim 1, wherein in step 2), the fluorinating is conducted at a temperature of 350° C., a space velocity of 220 $h^{-1}$, and a molar ratio of the HF gas phase to the 1,2-dichloro-3,3-difluoropropene as 4:1.

* * * * *